United States Patent [19]

Meier et al.

[11] Patent Number: 5,658,934

[45] Date of Patent: Aug. 19, 1997

[54] ARYL-SUBSTITUTED ALKOXYCARBONYL-1,4-DIHYDROPYRIDINE-5-CARBOXYLIC ACID ESTERS

[75] Inventors: Heinrich Meier, Higashi-Nada-ku, Japan; Wolfgang Hartwig, Stamford, Conn.; Bodo Junge, Wuppertal, Germany; Ulrich Niewöhner, Wermelskirchen, Germany; Rudolf Schohe-Loop, Wuppertal, Germany; Zhan Gao, Beijing, Switzerland; Bernard Schmidt, Lindlar; Maarten de Jonge, Overath, both of Germany; Teunis Schuurman, Brummen, Netherlands

[73] Assignee: Bayer Aktiengesellschaft, Leverkusen, Germany

[21] Appl. No.: 349,753

[22] Filed: Dec. 5, 1994

[30] Foreign Application Priority Data

Dec. 10, 1993 [DE] Germany ............... 43 42 193.8

[51] Int. Cl.$^6$ ............... C07D 211/86; A61K 31/455
[52] U.S. Cl. ............... 514/356; 546/321
[58] Field of Search ............... 546/321; 514/356

[56] References Cited

U.S. PATENT DOCUMENTS

| | | | |
|---|---|---|---|
| 3,488,359 | 1/1970 | Bossert | 546/321 |
| 3,574,843 | 4/1971 | Bossert | 546/321 |
| 3,966,946 | 6/1976 | Roe et al. | 514/356 |
| 4,044,141 | 8/1977 | Bossert et al. | 546/321 |
| 4,406,906 | 9/1983 | Meyer et al. | 514/356 |
| 4,419,518 | 12/1983 | Kamibayashi et al. | 546/279 |
| 4,510,310 | 4/1985 | Wehinger et al. | 546/321 |
| 4,559,350 | 12/1985 | Wehinger et al. | 514/332 |
| 4,568,681 | 2/1986 | Wehinger et al. | 514/332 |
| 4,622,332 | 11/1986 | Wehinger et al. | 514/356 |
| 4,727,066 | 2/1988 | Sunkel et al. | 546/321 |
| 4,761,420 | 8/1988 | Genain | 514/336 |
| 4,849,433 | 7/1989 | Wehinger et al. | 514/256 |
| 4,988,717 | 1/1991 | Wehinger et al. | 546/321 |

FOREIGN PATENT DOCUMENTS

| | | |
|---|---|---|
| 0012180 | 6/1980 | European Pat. Off. . |
| 0494816 | 7/1992 | European Pat. Off. . |
| 0525568 | 2/1993 | European Pat. Off. . |
| 3816361 | 12/1988 | Germany . |

OTHER PUBLICATIONS

CA 110:71311c, Glossmann et al. 1989.

CA 170710s, Roe et al. 1975.

Appel, Current Neurology vol. 6, pp. 289, 314, 315, Year Book Medical Publishers Inc. 1987.

Clark et al. Principles of Psychopharmacology pp. 166,167, Academic Press 1970.

Rampe D.R., et al., Can. Journ. Physiol. Pharmacol. 65, (1987), 1452–1460.

*Primary Examiner*—Jane Fan
*Attorney, Agent, or Firm*—Sprung Horn Kramer & Woods

[57] ABSTRACT

The invention relates to new aryl-substituted alkoxycarbonyl-1,4-dihydropyridine-5-carboxylic acid esters, processes for their preparation and their use in medicaments, in particular as agents having a cerebral action.

8 Claims, No Drawings

ARYL-SUBSTITUTED ALKOXYCARBONYL-1,4-DIHYDROPYRIDINE-5-CARBOXYLIC ACID ESTERS

The invention relates to new aryl-substituted alkoxycarbonyl-1,4-dihydropyridine-5-carboxylic acid esters, processes for their preparation and their use in medicaments, in particular as agents having a cerebral action.

The compound nimodipine and its cerebral activity is known [compare German Offenlegungsschrift 28 15 578]. Aryl-substituted dihydropyridines are also included as coronary and blood pressure agents by general substituent definitions in the description of German Offenlegungsschrift 2 508 181. The selected new compounds according to the invention are distinguished by their unexpectedly advantageous cerebral action.

The present invention relates to new aryl-substituted alkoxycarbonyl-1,4-dihydropyridine-5-carboxylic acid esters of the general formula (I)

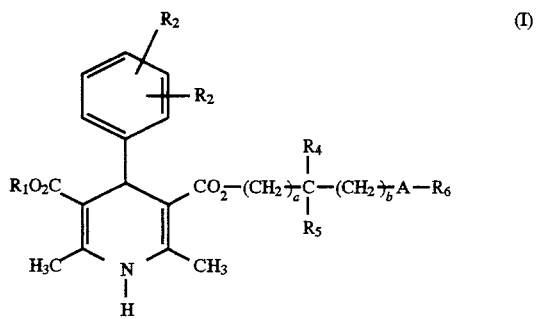

in which $R^1$ represents straight-chain or branched alkyl having up to 8 carbon atoms, which is optionally substituted by straight-chain or branched alkoxy having up to 6 carbon atoms, benzoyl or cycloalkyl having from 3 to 8 carbon atoms, or represents benzyl or cycloalkyl having 3 to 8 carbon atoms, $R^2$ represents halogen, trifluoromethyl or cyano, $R^3$ has the abovementioned meaning of $R^2$ and is identical to or different from this, or represents hydrogen, a and b are identical or different and represent the number 0, 1, 2, 3 or 4, $R^4$ and $R^5$ are identical or different and represent hydrogen, straight-chain or branched alkyl having up to 6 carbon atoms or phenyl, A represents an oxygen atom or represents a radical of the formula —CO—O—, —O—CO—, —NH—CO— or —CO—, $R^6$ represents a 5- to 7-membered, saturated or unsaturated heterocyclic radical having up to 3 hetero atoms from the series consisting of N, S and/or O, or represents benzyl, which is optionally substituted by halogen, or represents aryl having 6 to 10 carbon atoms, which is optionally substituted up to 3 times in an identical or different manner by halogen, phenyl or nitro or by straight-chain or branched alkoxy having up to 4 carbon atoms, and salts thereof.

A heterocyclic radical in general represents a 5- to 7-membered, preferably 5- to 6-membered unsaturated ring which can contain as hetero atoms up to 2 oxygen, sulphur and/or nitrogen atoms. 5- and 6-membered rings having one oxygen, sulphur and/or up to 2 nitrogen atoms are preferred.

Rings which are mentioned as being preferred are: thienyl, furyl, pyrrolyl, pyridyl or pyrimidyl.

The compounds according to the invention exist in stereoisomeric forms which either behave as mirror images (enantiomers) or do not behave as mirror images (diastereomers). The invention relates both to the antipodes and to the racemic forms as well as to the diastereomer mixtures. The racemic forms, like the diastereomers, can be separated into the stereoisomerically uniform constituents in a known manner (compare E. L. Eliel, Stereochemistry of Carbon Compounds, McGraw Hill, 1962).

Preferred compounds of the general formula (I) are those in which $R^1$ represents straight-chain or branched alkyl having up to 6 carbon atoms, which is optionally substituted by straight-chain or branched alkoxy having up to 4 carbon atoms or benzoyl, cyclopropyl, cyclopentyl or cyclohexyl, or represents benzyl, cyclopentyl, cyclohexyl or cycloheptyl, $R^2$ represents fluorine, chlorine, bromine, trifluoromethyl or cyano, $R^3$ has the abovementioned meaning of $R^2$ and is identical to or different from this, or represents hydrogen, a and b are identical or different and represent the number 0, 1, 2 or 3, $R^4$ and $R^5$ are identical or different and represent hydrogen, straight-chain or branched alkyl having up to 4 carbon atoms or phenyl, A represents an oxygen atom or represents a radical of the formula —CO—O—, —O—CO—, —NH—CO— or —CO—, $R^6$ represents pyridyl or benzyl, which are optionally substituted by fluorine, chlorine or bromine, or represents phenyl, which is optionally substituted up to 3 times in an identical or different manner by fluorine, chlorine, bromine, phenyl, methoxy or nitro, and salts thereof.

Particularly preferred compounds of the general formula (I) are those in which $R^1$ represents straight-chain or branched alkyl having up to 4 carbon atoms, which is optionally substituted by methoxy, benzoyl, cyclopropyl, cyclopentyl or cyclohexyl, or represents benzyl, cyclopentyl, cyclohexyl or cycloheptyl, $R^2$ represents fluorine, chlorine, trifluoromethyl or cyano, $R^3$ has the abovementioned meaning of $R^2$ and is identical to or different from this, or represents hydrogen, a and b are identical or different and represent the number 0, 1, 2 or 3, $R^4$ and $R^5$ are identical or different and represent hydrogen, methyl or phenyl, A represents an oxygen atom or represents a radical of the formula —CO—O—, —O—CO—, —NH—CO— or —CO—, $R^6$ represents benzyl or represents phenyl, which is optionally substituted up to 3 times in an identical or different manner by fluorine, chlorine, phenyl, methoxy or nitro, and salts thereof.

The following compounds of the general formula (I) are especially preferred:

2-isopropyl2-phenoxyethyl4-(3-cyanophenyl)-1,4-dihydro-2,6-dimethylpyridine-3,5-dicarboxylate bis-(2-phenoxyethyl) 4-(3-cyanophenyl)-1,4-dihydro-2,6-dimethylpyridine-3,5-dicarboxylate cyclopentyl 2-phenoxyethyl 4-(3-cyanophenyl)-1,4-dihydro-2,6-dimethylpyridine-3,5-dicarboxylate isopropyl 2-phenoxyethyl 4-(2-chloro-3-cyanophenyl)-1,4-dihydro-2,6-dimethylpyridine-3,5-dicarboxylate 2-benzoyloxyethyl isopropyl 4-(2,3-dichlorophenyl)-1,4-dihydro-2,6-dimethylpyridine-3,5-dicarboxylate 2-benzoyloxyethyl methyl 4-(2-fluorophenyl)-1,4-dihydro-2,6-dimethylpyridine-3,5-dicarboxylate 2-benzoyloxyethyl methyl 4-(2,3-difluorophenyl)-1,4-dihydro-2,6-dimethylpyridine-3,5-dicarboxylate 1,1-dimethylethyl 2-phenoxyethyl 4-(2,6-difluoro)-1,4-dihydro-2,6-dimethylpyridine-3,5-dicarboxylate cyclopentyl 2-benzyloxyethyl 4-(2,3-difluorophenyl)-1,4-dihydro-2,6-dimethylpyridine-3,5-dicarboxylate 2-benzoyloxyethyl isopropyl 4-(2-chlorophenyl)-1,4-dihydro-2,6-dimethylpyridine-3,5-dicarboxylate isopropyl 2-phenoxyethyl 4-(2,5-difluorophenyl)-1,4-dihydro-2,6-dimethylpyridine-3,5-dicarboxylate isopropyl 3-phenoxypropyl 4-(2,5-difluorophenyl)-1,4-dihydro-2,6-dimethylpyridine-3,5-dicarboxylate Processes have also been found for the preparation of the compounds of the general formula (I) according to the invention, characterized in that

[A] in the case where A represents an oxygen atom or the —CO— or —CO—O— group, compounds of the general formula (II)

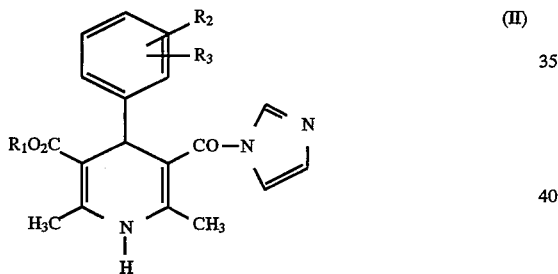

(II)

in which $R^1$, $R^2$ and $R^3$ have the abovementioned meaning, are reacted with compounds of the general formula (III)

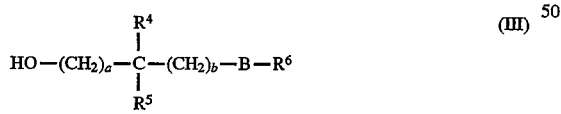

(III)

in which $R^4$, $R^5$, $R^6$, a and b have the abovementioned meaning and

B represents an oxygen atom or represents the —CO— group or represents the —CO—O— group, in inert solvents, if appropriate in the presence of a base, or

[B] in the case where A represents the —O—CO— group or —NH—CO— group, compounds of the general formula (IV)

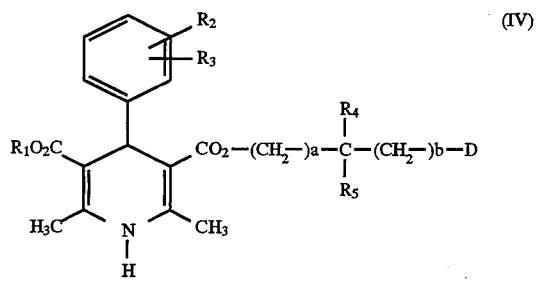

(IV)

in which $R^1$, $R^2$, $R^3$, $R^4$, $R^5$, a and b have the abovementioned meaning and D represents the $NH_2$ or OH group, are reacted with compounds of the general formula (V)

(V)

in which $R^6$ has the abovementioned meaning and

E, depending on the particular meaning of D, represents halogen, preferably chlorine, or represents hydroxyl, in inert solvents, if appropriate in the presence of a base and/or an auxiliary, or

[C] in the case where a and b represent the number 0 and A represents the —CO— group, compounds of the general formula (VI)

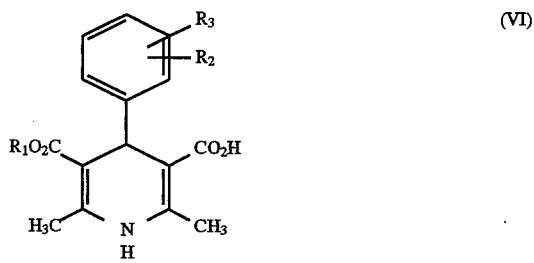

(VI)

in which $R^1$, $R^2$ and $R^3$ have the abovementioned meaning are reacted in inert solvents, if appropriate in the presence of a base and/or an auxiliary, with compounds of the general formula (VII)

(VII)

in which $R^6$ has the abovementioned meaning and

X represents chlorine, bromine, iodine, tosyloxy or mesyloxy, and in the case of the pure enantiomers, diastereomer mixtures of the general formula (VIII)

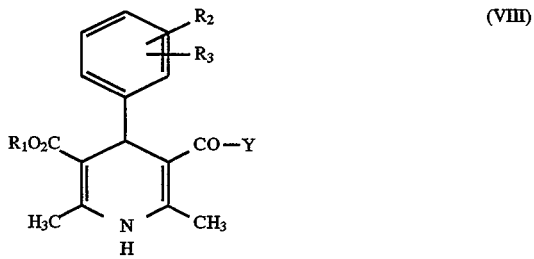

(VIII)

in which

R¹, R² and R³ have the abovementioned meanings and

Y represents a chiral alkoxy radical, are separated by customary methods, and the enantiomerically pure carboxylic acid is then prepared by selective hydrolysis and converted into the enantiomerically pure dihydropyridines by esterification with the corresponding alcohols.

The processes according to the invention can be illustrated by way of example by the following equation:

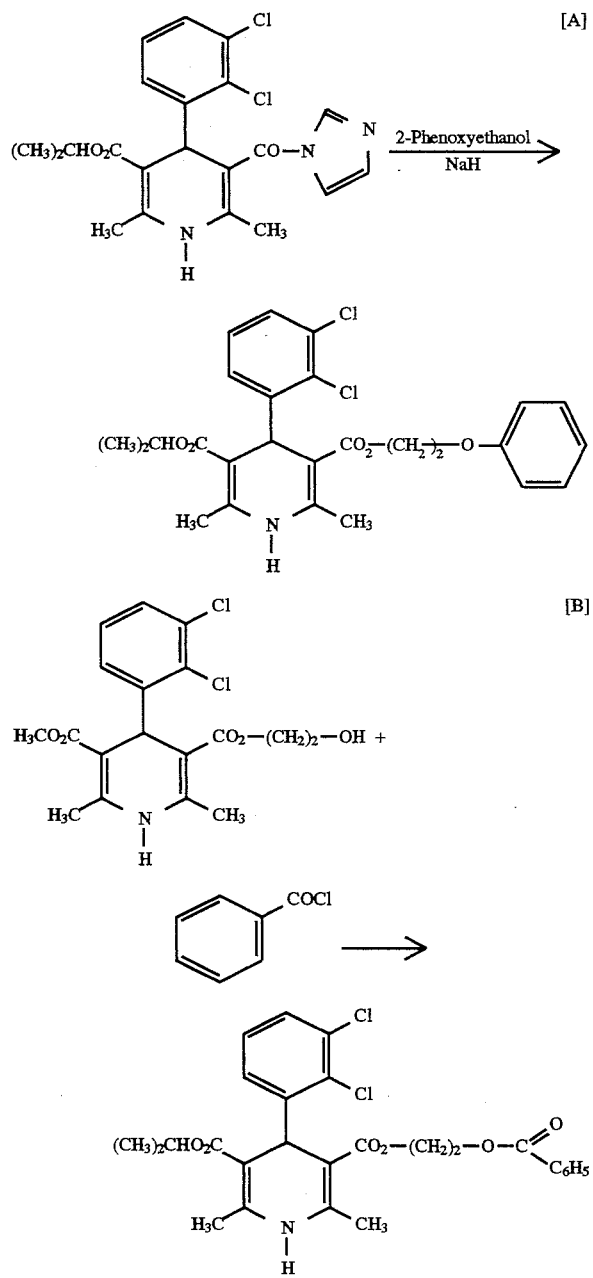

Solvents for processes [A], [B] and [C] according to the invention can be inert organic solvents which do not change under the reaction conditions. These include, preferably, ethers, such as, for example, diethyl ether, dioxane, tetrahydrofuran and glycol mono- or dimethyl ether, halogenated hydrocarbons, such as methylene chloride, chloroform or carbon tetrachloride, dichloroethylene and trichloroethylene, ethyl acetate, toluene, acetonitrile, hexamethylphosphoric acid triamide and acetone. It is of course possible to employ mixtures of the solvents. Tetrahydrofuran and methylene chloride are preferred.

The auxiliaries employed are preferably condensation agents, which can also be bases. Preferred condensation agents here are the customary condensation agents, such as carbodiimides, for example N,N'-diethyl-, N,N'-dipropyl-, N,N'-diisopropyl- and N,N'-dicyclohexylcarbodiimide and N-(3-dimethylaminoisopropyl)-N'-ethylcarbodiimide hydrochloride, or carbonyl compounds, such as carbonyldiimidazole, or 1,2-oxazolium compounds, such as 2-ethyl-5-phenyl-1,2-oxazolium 3-sulphonate or 2-tert-butyl-5-methyl-isoxazolium perchlorate, or acylamino compounds, such as 2-ethoxy-1-ethoxycarbonyl-1,2-dihydroquinoline, or propanephosphonic acid anhydride, or isobutyl chloroformate, or benzotriazolyloxy-tris (dimethylamino)phosphonium hexafluorophosphonate. N,N'-Dicyclohexylcarbodiimide and carbonyldiimidazole are preferred.

Suitable bases are in general alkali metal carbonates or hydrides, such as, for example, sodium carbonate or potassium carbonate or sodium hydride, or organic bases, such as trialkylamines, for example triethylamine, N-ethylmorpholine, N-methylpiperidine or diisopropylethylamine, or dimethylaminopyridine, 1,8-diazabicyclo[5.4.0]undec-7-ene (DBU) or 1,5-diazabicyclo[4.3.0]non-5-ene (DBN). Dimethylaminopyridine and sodium hydride are preferred.

The base is in general employed in an amount of 0.01 mol to 1 mol, preferably 0.05 mol to 0.1 mol, in each case per mol of the compounds of the general formulae (II), (IV) and (VI).

The auxiliaries are in general employed in an amount of 1 mol to 3 mol, preferably 1 mol to 1.5 mol, in each case per mol of the compounds of the general formulae (II), (IV) and (VI).

The reaction temperature for processes [A], [B] and [C] can be varied within a relatively wide range. In general, the reaction is carried out in a range from −20° C. to 200° C., preferably 0° C. to 25° C.

The processes can be carried out under normal pressure or increased or reduced pressure (for example 0.5 to 5 bar), preferably under normal pressure.

The substances participating in the reaction can be employed in any desired ratio in carrying out the process according to the invention. In general, however, molar amounts of the reactants are used.

In the reaction of the compounds of the general formulae (II) or (IV) with the compounds of the general formulae (III) or (V), the latter are employed in twice the molar amount per mol of the compounds of the general formulae (II) or (IV).

The customary reagents are suitable for activation of the carboxylic acid, such as inorganic halides, for example thionyl chloride, phosphorus trichloride or phosphorus pentachloride, or carbonyldiimidazole, carbodiimides, such as cyclohexylcarbodiimide or 1-cyclohexyl-3-[2-(N-methylmorpholino)ethyl]-carbodiimide p-toluenesulphonate, or N-hydroxyphthalimide or N-hydroxy-benzotriazole.

Enantiomerically pure forms, furthermore, are obtained, for example, by separating diastereomer mixtures of the compounds of the general formula (I), in which R² or R³ represents a chiral ester radical, by a customary method, and the enantiomerically pure-carboxylic acids are subsequently prepared and then converted into the enantiomerically pure dihydropyridines, if appropriate by esterification with corresponding alcohols.

Suitable chiral ester radicals are all the esters of enantiomerically pure alcohols, such as, for example, 2-butanol, 1-phenylethanol, lactic acid, lactic acid esters, mandelic acid, mandelic acid esters, 2-amino-alcohols, sugar derivatives and many other enantiomerically pure alcohols.

The diastereomers are in general separated either by fractional crystallization, by column chromatography or by Craig partition. The optimum process must be decided upon from case to case, and sometimes it is also expedient to use combinations of the individual processes. Separation by crystallization or Craig partition or a combination of both processes is particularly suitable.

The enantiomerically pure dihydropyridines are esterified by customary methods after activation of the carboxylic acid (for example as the imidazolide).

The separation of the enantiomers is preferably carried out by column chromatography by the customary method, the columns being packed with chiral support materials.

The above preparation processes are given merely for illustration. The preparation of the compounds of the formula (I) is not limited to these processes, but any modification of these processes can be used in the same manner for the preparation of the compounds according to the invention.

The compounds of the general formulae (II) to (VIII) are known or can be prepared by customary methods.

The compounds according to the invention show an unforeseeable, useful pharmacological action spectrum.

The compounds according to the invention are calcium channel ligands having selectivity for L-type calcium channels of the central nervous system. This selectivity can be demonstrated, for example, by comparison of the binding affinities for DHP binding sites in the rat brain and rat heart.

The compounds positively influence learning and memory performance, as demonstrated by their performance-improving action in typical learning and memory models, such as the water labyrinth, Morris labyrinth, passive avoidance or reminiscence tests in automated Skinner boxes. They have an antidepressant potential, as their activity in the Porsolt rat swimming test shows.

Binding assays:

The binding affinities for PN 200-110 binding sites in rat brains and rat hearts are determined by the method of Rampe D. R., Mutledge A., Janis R. A., Triggle D. J.: Can. Journ. Physiol. Pharmacol. 65 (1987) 1452.

Water labyrinth:

Elderly Wistar rats are placed at the start position in a plastic tank filled with cold water and divided by vertical barriers. To arrive at a ladder which allows the animals to escape from the water, they must swim around these barriers. The time required to discover the exit and the number of errors on the route thereto are recorded. An error is defined as swimming into a dead end or swimming over the boundary line of imaginary squares, into which the tank is divided, in the direction away from the exit.

The rats remain in the labyrinth until they find the exit, but for no longer than 300 seconds. They are then picked up, dried and warmed under a red lamp. Thereafter, they return to their home cage.

In a typical experiment, two equivalent groups of animals (placebo and test substance, in each case n=15) are determined by a preliminary test. The animals then undergo 6 test sessions, two per day. The test substances or placebo are administered perorally 30 minutes before the experiments. The shortening in time before the exit is reached, the reduction in the number of errors and the increase in the number of animals which find the exit at all are a measure of the learning- and memory-improving action of the test substances in comparison with placebo.

Porsolt rat swimming test

During a preliminary test, young rats are placed in a glass cylinder (40 cm high, 20 cm diameter) filled 17 cm high with water at 25° C. After 20 minutes in the water, the animals are taken out and warmed under a lamp for 30 minutes. In this preliminary test, all the rats attempt to escape from the cylinder until they remain immobile after about 15 minutes ("behavioural despair"). 24 hours later, the test session starts, in which the rats are placed in the glass cylinder as on the previous day, but this time for only 5 minutes. The periods of time which the rats remain immobile during these 5 minutes are recorded. A rat which performs only minimal movements to keep its head above water while holding itself upright in the water is regarded as immobile. The antidepressant action of the test substances manifests itself in a reduction of the period of immobility in comparison with the placebo values.

On the basis of their pharmacological properties, the compounds according to the invention can be employed for the preparation of medicaments for the treatment of centrally degenerative diseases, such as, for example, occurrences with dementias (multi-infarct dementia MID, primary degenerative dementia PDD, presenile and senile Alzheimer's disease, HIV dementia and other forms of dementia), Parkinson's disease or amyotrophic lateral sclerosis.

The active compounds furthermore are suitable for the treatment of disturbances in cerebral performance in old age, organic brain syndrome (OBS) and age-associated memory impairment (AAMI).

They are useful for the prophylaxis of and for combating the consequences of disturbances in cerebral circulation, such as cerebral ischaemias, apoplexies and subarachnoid haemorrhages.

They are suitable for the treatment of depressions and of mania. Other fields of use are the treatment of migraine, of neuropathies and of addictions and withdrawal symptoms.

The present invention also relates to pharmaceutical formulations which, in addition to inert, non-toxic, pharmaceutically suitable auxiliaries and excipients, contain one or more compounds of the general formula (I), or which comprise one or more active compounds of the formula (I), and to processes for the preparation of these formulations.

The active compounds of the formula (i) are to be present in these formulations in a concentration of 0.1 to 99.5% by weight, preferably 0.5 to 95% by weight of the total mixture.

In addition to the active compounds of the formula (I), the pharmaceutical formulations can also contain other pharmaceutical active compounds.

The abovementioned pharmaceutical formulations can be prepared in the customary manner by known methods, for example with the auxiliaries or excipients.

In general, it has proved advantageous to administer the active compound or compounds of the formula (I) in total amounts of about 0.01 to about 70 mg/kg, preferably in total amounts of about 0.1 mg/kg to 20 mg/kg of body weight every 24 hours, if appropriate in the form of a plurality of individual doses, to achieve the desired results.

However, it may be advantageous, where appropriate, to deviate from the amounts mentioned, in particular as a function of the nature and body weight of the subject to be treated, of the behaviour of the individual towards the medicament, of the nature and severity of the disease, of the nature of the formulation and administration, and of the time or interval at which administration takes place.

Unless noted otherwise, the particular $R_f$ values listed were determined by thin layer chromatography on silica gel (aluminium foil, silica gel 60 F 254, E. Merck). The substance spots were visualized by observation under UV light and/or by spraying with 1% strength potassium permanganate solution.

The flash chromatography was carried out on silica gel 60, 0.040-0.064 mm, E. Merck. Elution with solvent gradients means: starting with the pure, non-polar solvent mixture component, the polar mobile phase component is admixed in an increasing extent until the desired product is eluted (monitoring by thin layer chromatography).

PREPARATION EXAMPLES

Example 1

Methyl 5-[2-(benzoyloxy)-ethoxycarbonyl]-2,6-dimethyl-4-(2,3-dichlorophenyl)-1,4-dihydropyridine-3-carboxylate

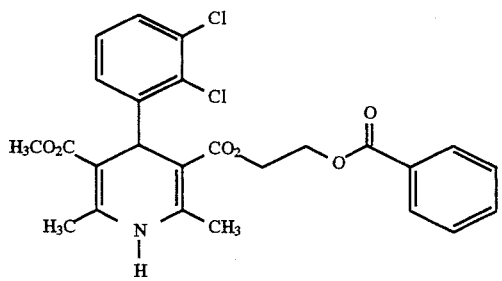

1.4 g (10 mmol) of benzoyl chloride in 10 ml of absolute $CH_2Cl_2$ are added dropwise to 4.0 g (10 mmol) of methyl 5-(2-hydroxyethyloxycarbonyl)-2,6-dimethyl-4-(2,3-dichlorophenyl)-1,4-dihydropyridine-3-carboxylate and 1.12 g (11 mmol) of triethylamine in 20 ml of absolute methylene chloride ($CH_2Cl_2$) at room temperature and the mixture is stirred for 3–5 hours (monitoring by thin layer chromatography). The organic phase is filtered off, washed with 1N HCl, saturated $NaHCO_3$ solution and saturated NaCl solution, dried over $Na_2SO_4$ and evaporated. The residue is purified by chromatography over silica gel (eluent: toluene/ethyl acetate 4:1).

Yield: 5.74 g $R_f$=0.49 (toluene/ethyl acetate 1:1)

The compounds listed in Table 1 are prepared analogously to the instructions of Example 1:

TABLE 1

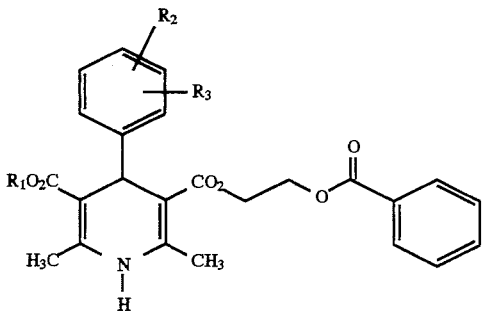

| Example No. | $R^1$ | $R^2$ | $R^3$ | Yield (% of theory) | $R_f$ value* |
|---|---|---|---|---|---|
| 2 | —CH(CH₃)₂ | 2-Cl | 3-Cl | 57.4 | 0.19[a] |
| 3 | —CH₃ | H | 3-CN | 66.3 | 0.13[a] |
| 4 | —CH₃ | 2-F | H | 63.3 | 0.15[a] |

TABLE 1-continued

| Example No. | $R^1$ | $R^2$ | $R^3$ | Yield (% of theory) | $R_f$ value* |
|---|---|---|---|---|---|
| 5 | —CH₃ | 2-F | 3-F | 60.7 | 0.13[a] |
| 6 | —CH(CH₃)₂ | 2-F | 6-F | 58.4 | 0.28[a] |
| 7 | —C(CH₃)₃ | 2-Cl | 3-Cl | 76.4 | 0.59[b] |

[a]= toluene:ethyl acetate 5:1
[b]= toluene:ethyl acetate 1:1

Example 8

Isopropyl 5-(2-phenoxyethoxycarbonyl)-2,6-dimethyl-4-(2,3-dichlorophenyl)-1,4-dihydropyridine-3-carboxylate

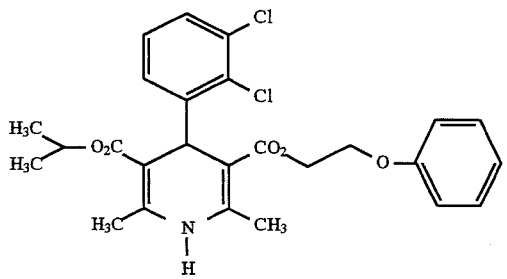

4.34 g (10 mmol) of 5-isopropoxycarbonyl-2,6-dimethyl-4-(2,3-dichlorophenyl)-1,4-dihydropyridine-3-carboxylic acid imidazolide, 1.66 g (12 mmol) of 2-phenoxyethanol and 360 mg (12 mmol) of sodium hydride (80% strength suspension) are stirred in 30 ml of absolute tetrahydrofuran at 40° C. for 1 hour (monitoring by thin layer chromatography). The solvent is distilled off in vacuo, the residue is taken up in 30 ml of ethyl acetate and the mixture is washed with 2N HCl solution and saturated NaCl solution. After the mixture has been dried over $Na_2SO_4$, it is evaporated and the residue is purified by chromatography over silica gel (eluent: toluene/ethyl acetate 10:1).

Yield: 1.94 g (38.5%)

$R_f$=0.22 (toluene/ethyl acetate 5:1)

The compounds listed in Table 2 are prepared analogously to the instructions of Example 8:

TABLE 2

*(structure: 1,4-dihydropyridine with aryl (R₂, R₃ substituents) at 4-position; $R_1O_2C$ and $CO_2-(CH_2)_a-CH_2-A-R_6$ at 3,5-positions; 2,6-dimethyl; NH)*

| Example No. | $R^1$ | $R^2$ | $R^3$ | a | A | $R^6$ | Yield (% of theory) | $R_f$* |
|---|---|---|---|---|---|---|---|---|
| 9 | $(CH_3)_3C-$ | 2-Cl | 3-Cl | 1 | $-CO-O-$ | $-CH_2-C_6H_5$ | 64.2 | 0.64 |
| 10 | $(CH_3)_2-CH-$ | 2-Cl | 3-Cl | 3 | $-O-$ | $-CH_2-C_6H_5$ | 58.8 | 0.25 |
| 11 | $(CH_3)_2-CH-$ | 2-Cl | 3-Cl | 1 | $-O-$ | 4-$C_6H_5$-$C_6H_4$- | 66.9 | 0.18 |
| 12 | $(CH_3)_2-CH-$ | 2-Cl | 3-Cl | 2 | $-CO-$ | $-C_6H_5$ | 31.5 | 0.24 |
| 13 | $-CH_3$ | 2-Cl | 3-Cl | 1 | $-O-$ | $-CH_2-C_6H_5$ | 46.7 | 0.31 |
| 14 | cyclopentyl | 2-Cl | H | 1 | $-O-$ | $-C_6H_5$ | 59.1 | 0.43 |
| 15 | $(CH_3)_2CH-$ | 2-Cl | H | 1 | $-O-$ | $-C_6H_5$ | 32.5 | 0.37 |
| 16 | $-CH_2-C_6H_{11}$ | 2-Cl | 3-Cl | 1 | $-O-$ | $-CH_2-C_6H_5$ | 40.0 | 0.44 |
| 17 | $-CH_3$ | 2-Cl | 3-Cl | 1 | $-O-$ | $-C_6H_5$ | 59.8 | 0.26 |
| 18 | cyclopentyl | 2-Cl | 3-Cl | 1 | $-O-$ | $-C_6H_5$ | 63.2 | 0.43 |
| 19 | $-CH_3$ | 2-Cl | 3-Cl | 1 | $-O-$ | $-C_6H_5$ | 53.5 | 0.31 |
| 20 | cyclopentyl | 2-Cl | 3-Cl | 1 | $-O-$ | $-C_6H_5$ | 49.1 | 0.41 |
| 21 | cyclopentyl | 2-Cl | 3-Cl | 1 | $-O-$ | $-CH_2-C_6H_5$ | 52.4 | 0.42 |
| 22 | $C_6H_5-CH_2-$ | 2-Cl | 3-Cl | 2 | $-O-$ | $-C_6H_5$ | 36.3 | 0.43 |
| 23 | $C_6H_5-CH_2-$ | 2-Cl | 3-Cl | 1 | $-O-$ | $-C_6H_5$ | 52.1 | 0.42 |
| 24 | cycloheptyl | 2-Cl | 3-Cl | 2 | $-O-$ | $-C_6H_5$ | 57.4 | 0.46 |
| 25 | cycloheptyl | 2-Cl | 3-Cl | 1 | $-O-$ | $-C_6H_5$ | 45.0 | 0.44 |

TABLE 2-continued

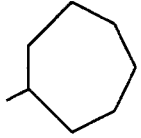

| Example No. | R¹ | R² | R³ | a | A | R⁶ | Yield (% of theory) | $R_f$* |
|---|---|---|---|---|---|---|---|---|
| 26 | cycloheptyl | 2-Cl | 3-Cl | 1 | —O— | $CH_2-C_6H_5$ | | M.p. 102° C. |
| 27 | cycloheptyl | 2-Cl | H | 1 | —O— | $CH_2-C_6H_5$ | | 114° C. |

*= toluene: ethyl acetate = 5:1

The compounds listed in Table 3 are prepared analogously to the instructions of Examples 1 and 8:

TABLE 3

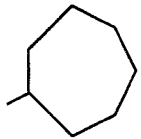

| Example No. | R¹ | R² | R³ | a | A | R⁶ | $R_f$*/Melting point °C. |
|---|---|---|---|---|---|---|---|
| 28 | $-CH(CH_3)_2$ | 2-Cl | -6-F | 1 | —O— | $-C_6H_5$ | 0.27$^c$ |
| 29 | cyclopentyl | 2-Cl | -6-F | 1 | —O— | $-C_6H_5$ | 0.36$^d$ |
| 30 | $-CH_3$ | 3-CN | H | 1 | —O— | $-C_6H_5$ | 148–149 |
| 31 | $-CH(CH_3)_2$ | 3-CN | H | 1 | —O— | $-C_6H_5$ | 140 |
| 32 | $-CH(CH_3)_2$ | 3-CN | H | 1 | —O— | $-C_6H_5$-p-F | 114–15 |
| 33 | $-CH(CH_3)_2$ | 3-CN | H | 1 | —O— | $-C_6H_5$-o-$OCH_3$ | 146 |
| 34 | $-CH(CH_3)_2$ | 3-CN | H | 1 | —O—CO— | $-C_6H_5$ | 102-3 |

TABLE 3-continued

Structure: 1,4-dihydropyridine with $R_1O_2C$-, $CO_2$-$(CH_2)_a$-$CH_2$-$A$-$R_6$ substituents, 2,6-dimethyl, N-H, and 4-aryl with $R_2$, $R_3$ substituents.

| Example No. | $R^1$ | $R^2$ | $R^3$ | a | A | $R^6$ | $R_f$*/Melting point °C. |
|---|---|---|---|---|---|---|---|
| 35 | $-CH(CH_3)_2$ | 3-CN | H | 1 | $-O-CO-$ | 3,4,5-trimethoxyphenyl | 0.40$^e$ |
| 36 | $-C(CH_3)_3$ | 3-CN | H | 1 | $-O-$ | $-C_6H_5$ | 0.41$^f$ |
| 37 | $-C(CH_3)_3$ | 2-F | 3-F | 1 | $-O-CO-$ | $-C_6H_5$ | 131° C. |
| 38 | cyclopentyl | 3-CN | H | 1 | $-O-$ | $-C_6H_5$ | 174–176 |
| 39 | cyclopentyl | 3-CN | H | 1 | $-O-$ | $-C_6H_5$-p-F | 155–156 |
| 40 | cyclopentyl | 3-CN | H | 1 | $-O-$ | $-C_6H_5$-o-$OCH_3$ | 127–128 |
| 41 | cyclopentyl | 3-CN | H | 1 | $-O-CO-$ | $-C_6H_5$ | 87–90 |
| 42 | cyclopentyl | 3-CN | H | 1 | $-O-CO-$ | 3,4,5-trimethoxyphenyl | 119–121 |
| 43 | $-CH(CH_3)_2$ | 2-Cl | 3-CN | 1 | $-O-$ | $-C_6H_5$ | 154-5 |
| 44 | cyclopentyl | 2-F | 3-F | 1 | $-O-$ | $-CH_2-C_6H_5$ | 108–109.5 |
| 45 | $-CH(CH_3)_2$ | 2-F | 3-F | 1 | $-O-$ | $-CH_2-C_6H_5$ | 100 |
| 46 | $-CH(CH_3)_2$ | 2-F | 3-F | 1 | $-O-CO-$ | $-C_6H_5$ | 131 |
| 47 | $-(CH_2)_2-OCH_3$ | 3-F | 4-F | 1 | $-O-CO-$ | $-C_6H_5$ | 98 |
| 48 | $-CH(CH_3)_2$ | 3-CN | H | 1 | $-O-$ | $-C_6H_5$ | 140 |
| 49 | $-CH(CH_3)_2$ | 2-F | 5-F | 2 | $-O-$ | $-C_6H_5$ | 105° C. |
| 50 | $-Me$ | 2-F | 5-F | 2 | $-O-$ | $-C_6H_5$ | 76° C. |
| 51 | cyclopentyl | 2-F | 3-F | 1 | $-O-$ | $-C_6H_5$ | 167–168 |

TABLE 3-continued

| Example No. | $R^1$ | $R^2$ | $R^3$ | a | A | $R^6$ | $R_f$*/Melting point °C. |
|---|---|---|---|---|---|---|---|
| 52 | $-CH(CH_3)_2$ | 2-F | 3-F | 1 | $-O-$ | $-C_6H_5$ | 131 |
| 53 | $-CH(CH_3)_2$ | 2-F | 3-F | 2 | $-O-$ | $-C_6H_5$ | 106–108 |
| 54 | $CH_3$ | 2-F | 3-F | 1 | $-O-$ | $-C_6H_5$ | 111–112 |
| 55 | $-CH(CH_3)_2$ | 2-Cl | H | 1 | $-O-$ | $-CH_2C_6H_5$ | 119 |
| 56 | $CH_3O(CH_2)_2-$ | 2-Cl | H | 2 | $-O-$ | $-C_6H_5$ | 115 |
| 57 | $CH_3O(CH_2)_2-$ | 2-Cl | H | 1 | $-O-$ | $-CH_2C_6H_5$ | 121–122 |
| 58 | $CH_3O(CH_2)_2-$ | 2-Cl | H | 1 | $-O-$ | $-C_6H_5$ | 109 |
| 59 | cyclohexyl-$CH_2$ | 2-F | 3-F | 1 | $-O-$ | $-C_6H_5$ | 164–165 |
| 60 | cyclopentyl-$CH_2$ | 2-F | 3-F | 1 | $-O-$ | $-C_6H_5$ | 179–180 |
| 61 | $CH_3O(CH_2)_2-$ | 2-F | 3-F | 1 | $-O-$ | $-C_6H_5$ | 116–117 |
| 62 | $CH_3O(CH_2)_2$ | 2-F | 3-F | 2 | $-O-$ | $-C_6H_5$ | 106–107 |
| 63 | $CH_3O(CH_3)_2$ | 2-F | 3-F | 1 | $-O-$ | $-CH_2C_6H_5$ | 99–100 |
| 64 | $CH_3$ | 2-F | 3-F | 1 | $-O-$ | $-CH_2C_6H_5$ | 144–145 |

$^c$= methylene chloride/ethyl acetate 20:1
$^d$= toluene/ethyl acetate 10:1
$^e$= toluene/ethyl acetate 1:1
$^f$= toluene/ethyl acetate 3:1

Example 65

Cyclopentyl 2-phenoxyethyl 4-(2,5-difluorophenyl)-1,4-dihydro-2,6-dimethylpyridine-3,5-dicarboxylate

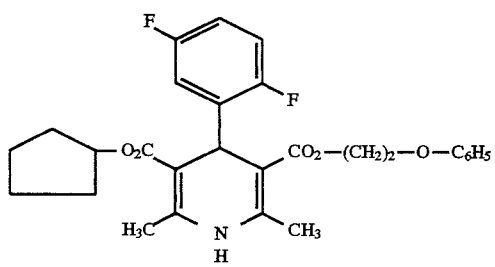

3.0 g (7.0 mmol) of 5-cyclopentyloxycarbonyl-2,6-dimethyl-4-(2,5-difluorophenyl)-1,4-dihydropyridine-3-carboxylic acid imidazolide are stirred in 30 ml of 2-phenoxyethanol at 150° C. for 2 hours. Excess phenoxyethanol is then distilled off under 0.1 mbar and the residue is purified by filtration over 100 ml of silica gel in toluene/ethyl acetate. The resulting crude product is crystallized from ether/petroleum ether. 2.8 g (80%) of the target compound of melting point 198° C. are obtained.

The compounds listed in Table 4 are prepared analogously to the instructions of Example 65:

TABLE 4

| Example No. | $R^1$ | $R^2$ | $R^3$ | a | A | $R^6$ | Melting point °C./$R_f$ |
|---|---|---|---|---|---|---|---|
| 66 | cyclohexyl | 2-Cl | 6-F | 1 | O | $-C_6H_5$ | 0.36$^a)$ |
| 67 | $-CH(CH_3)_2$ | 2-Cl | 6-F | 1 | O | $-C_6H_5$ | 0.27$^b)$ |
| 68 | $-CH(CH_3)_2$ | 2-F | 5-F | 1 | O | $-C_6H_5$ | 120 |

TABLE 4-continued

Structure with $RO_2C$, $CO_2-(CH_2)_a-CH_2-A-R_6$, $H_3C$, $CH_3$, N-H, and phenyl with $R_2$, $R_3$.

| Example No. | $R^1$ | $R^2$ | $R^3$ | a | A | $R^6$ | Melting point °C/$R_f$ |
|---|---|---|---|---|---|---|---| a) toluene/ethyl acetate 10:1
b) methylene chloride/ethyl acetate 20:1

Example 69

Methyl 2-oxo-2-phenylethyl 4-(2,3-dichlorophenyl)-1,4-dihydro-2,6-dimethylpyridine-3,5-dicarboxylate

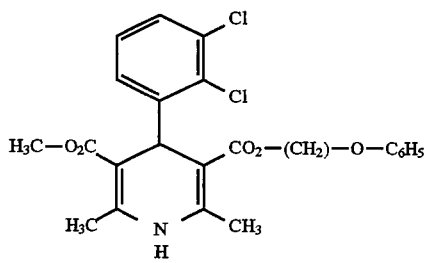

1.04 g (7.5 mmol) of potassium carbonate are added to a solution of 4.00 g (11.2 mmol) of 4-(2,3-dichlorophenyl)-1,4-dihydro-2,6-dimethyl-5-methoxycarbonylpyridine-3-carboxylic acid in dimethylformamide and the mixture is stirred at room temperature for 10 minutes. 2.66 g (13.4 mmol) of ω-bromoacetophenone, dissolved in a little dimethylformamide, are then added and the mixture is stirred at room temperature for a further 3 hours. The crude product obtained after aqueous working up is purified by crystallization from ether/petroleum ether. 2.8 g (90%) of the target compound of melting point 168°–170° C. are thus obtained.

The compounds listed in Table 5 are obtained analogously to the instructions of Example 69:

TABLE 5

Structure with $RO_2C$, $CO_2-CH_2-CO-R_6$, $H_3C$, $CH_3$, N-H, and phenyl with $R_2$, $R_3$.

| Example No. | $R^1$ | $R^2$ | $R^3$ | $R^6$ | Melting point °C. |
|---|---|---|---|---|---|
| 70 | $-CH_3$ | 2-Cl | 3-Cl | -C$_6$H$_4$-OCH$_3$ (para) | 199 |
| 71 | $-CH_3$ | 2-Cl | 3-Cl | -C$_6$H$_4$-Cl (para) | 179 |
| 72 | $-CH_3$ | 2-Cl | 3-Cl | -C$_6$H$_4$-NO$_2$ (para) | 220 |
| 73 | $-CH(CH_3)_2$ | 2-Cl | 3-Cl | -C$_6$H$_5$ | 146 |
| 74 | $-CH(CH_3)_2$ | 2-Cl | 3-Cl | -C$_6$H$_4$-OCH$_3$ (para) | 146–147 |
| 75 | $-CH(CH_3)_2$ | 2-Cl | 3-Cl | -C$_6$H$_4$-Cl (para) | 147 |
| 76 | $-CH(CH_3)_2$ | 2-Cl | 3-Cl | -C$_6$H$_4$-NO$_2$ (para) | 138–139 |
| 77 | cyclopentyl | 2-Cl | 3-Cl | -C$_6$H$_5$ | 163–164 |
| 78 | cyclopentyl | 2-Cl | 3-Cl | -C$_6$H$_4$-OCH$_3$ (para) | 137 |
| 79 | cyclopentyl | 2-Cl | 3-Cl | -C$_6$H$_4$-Cl (para) | 122 |
| 80 | cyclopentyl | 2-Cl | 3-Cl | -C$_6$H$_4$-NO$_2$ (para) | 167 |

Example 81

Bis-(2-phenoxyethyl) 4-(3-cyanophenyl)-1,4-dihydro-2,6-dimethylpyridine-3,5-dicarboxylate

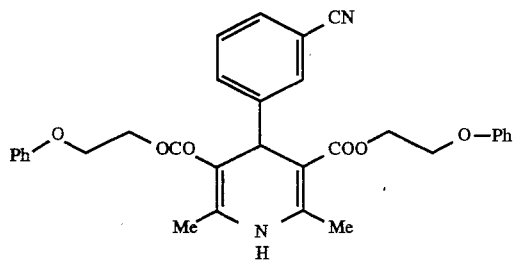

3.0 g (23 mmol) of 3-cyanobenzaldehyde, 5.0 g (23 mmol) of 2-phenoxyethylacetoacetate and 5.0 g (23 mmol) of 2-phenoxyethyl 3-aminocrotonate in 150 ml of 2-propanol are heated under reflux for 14 hours. The residue which remains after concentration is purified by flash chromatography (silica gel; toluene/ethyl acetate 3:1). After the crude product has been triturated with diethyl ether/cyclohexane (1:1), it is recrystallized from toluene/ethyl acetate (1:1). 4.2 g (34%) of colourless crystals of melting point 102°–103° C. are obtained.

The compounds listed in Table 6 are prepared analogously to the instructions of Example 81:

TABLE 6

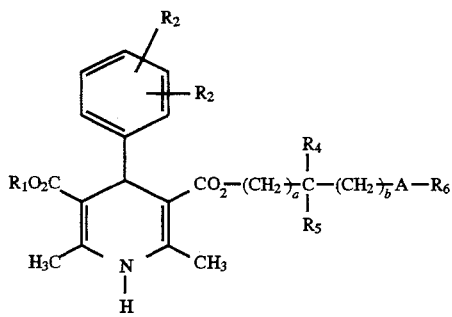

| Example No. | $R^2$ | $R^3$ | Melting point °C. |
|---|---|---|---|
| 82 | 2-Cl | 3-CN | 115–116 |
| 83 | 2-Cl | 3-Cl | 93–96 |
| 84 | 2-Cl | H | 123–124 |
| 85 | 2-F | 3-F | 113–114 |

We claim:

1. A compound of the formula $$(I)$$

in which $R^1$ represents straight-chain or branched alkyl having up to 8 carbon atoms, which is optionally substituted by straight-chain or branched alkoxy having up to 6 carbon atoms, benzoyl or cycloalkyl having from 3 to 8 carbon atoms, or represents benzyl or cycloalkyl having 3 to 8 carbon atoms, $R^2$ represents halogen, trifluoromethyl or cyano, $R^3$ has the abovementioned meaning of $R^2$ and is identical to or different from this, or represents hydrogen, a and b are identical or different and represent the number 0, 1, 2, 3 or 4, $R^4$ and $R^5$ and are identical or different and represent hydrogen, straight-chain or branched alkyl having up to 6 carbon atoms or phenyl, A represents a radical of the formula —CO—O—, —O—CO—, —NH—CO— or —CO—, $R^6$ represents benzyl, which is optionally substituted by halogen, or represents aryl having 6 to 10 carbon atoms, which is optionally substituted up to 3 times in an identical or different manner by halogen, phenyl or nitro or by straight-chain or branched alkoxy having up to 4 carbon atoms, or a salt thereof.

2. A compound according to claim 1, in which $R^1$ represents straight-chain or branched alkyl having up to 6 carbon atoms, which is optionally substituted by straight-chain or branched alkoxy having up to 4 carbon atoms or benzoyl, cyclopropyl, cyclopentyl or cyclohexyl, or represents benzyl, cyclopentyl, cyclohexyl or cycloheptyl, $R^2$ represents fluorine, chlorine, bromine, trifluoromethyl or cyano, $R^3$ has the abovementioned meaning of $R^2$ and is identical to or different from this, or represents hydrogen, a and b are identical or different and represent the number 0, 1, 2 or 3, $R^4$ and $R^5$ are identical or different and represent hydrogen, straight-chain or branched alkyl having up to 4 carbon atoms or phenyl, A represents a radical of the formula —CO—O—, —O—CO—, —NH—CO— or —CO—, $R^6$ represents benzyl, which is optionally substituted by fluorine, chlorine or bromine, or represents phenyl, which is optionally substituted up to 3 times in an identical or different manner by fluorine, chlorine, bromine, phenyl, methoxy or nitro, or a salt thereof.

3. A compound according to claim 1, in which $R^1$ represents straight-chain or branched alkyl having up to 4 carbon atoms, which is optionally substituted by methoxy, benzoyl, cyclopropyl, cyclopentyl or cyclohexyl, or represents benzyl, cyclopentyl, cyclohexyl or cycloheptyl, $R^2$ represents fluorine, chlorine, trifluoromethyl or cyano, $R^3$ has the abovementioned meaning of $R^2$ and is identical to or different from this, or represents hydrogen, a and b are identical or different and represent the number 0, 1, 2 or 3, $R^4$ and $R^5$ are identical or different and represent hydrogen, methyl or phenyl, A represents a radical of the formula —CO—O—, —O—CO—, —NH—CO— or —CO—

$R^6$ represents benzyl or represents phenyl, which is optionally substituted up to 3 times in an identical or different manner by fluorine, chlorine, phenyl, methoxy or nitro, or a salt thereof.

4. A pharmaceutical composition which comprises a pharmaceutically effective amount of a compound according to claim 1 and a pharmaceutically acceptable auxiliary or excipient.

5. A method for treating dementia which comprises administering to a patient in need thereof an effective amount of a compound of the formula

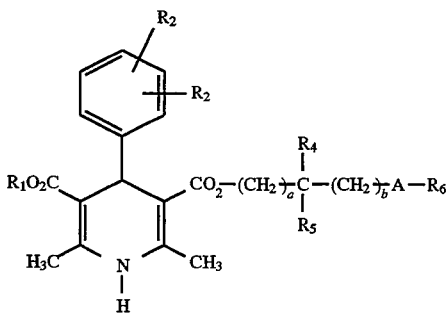

in which $R^1$ represents straight-chain or branched alkyl having up to 8 carbon atoms, which is optionally substituted by straight-chain or branched alkoxy having up to 6 carbon atoms, benzoyl or cycloalkyl having from 3 to 8 carbon atoms, or represents benzyl or cycloalkyl having 3 to 8 carbon atoms, $R^2$ represents halogen, trifluoromethyl or cyano, $R^3$ has the abovementioned meaning of $R^2$ and is identical to or different from this, or represents hydrogen, a and b are identical or different and represent the number 0, 1, 2, 3 or 4, $R^4$ and $R^5$ are identical or different and represent hydrogen, straight-chain or branched alkyl having up to 6 carbon atoms or phenyl, A represents a radical of the formula —CO—O—, —O—CO—, —NH—CO— or —CO—, $R^6$ represents benzyl, which is optionally substituted by halogen, on represents aryl having 6 to 10 carbon atoms, which is optionally substituted up to 3 times in an identical or different manner by halogen, phenyl or nitro or by straight-chain or branched alkoxy having up to 4 carbon atoms, or a salt thereof.

6. The method according to claim 5, wherein in the compound of formula (I)

$R^1$ represents straight-chain or branched alkyl having up to 6 carbon atoms, which is optionally substituted by straight-chain or branched alkoxy having up to 4 carbon atoms or benzoyl, cyclopropyl, cyclopentyl or cyclohexyl, or represents benzyl, cyclopentyl, cyclohexyl or cycloheptyl, $R^2$ represents fluorine, chlorine, bromine, trifluoromethyl or cyano, $R^3$ has the abovementioned meaning of $R^2$ and is identical to or different from this, or represents hydrogen, a and b are identical or different and represent the number 0, 1, 2 or 3, $R^4$ and $R^5$ are identical or different and represent hydrogen, straight-chain or branched alkyl having up to 4 carbon atoms or phenyl, A represents a radical of the formula —CO—O—, —O—CO—, —NH—CO— or —CO—, $R^6$ represents benzyl, which is optionally substituted by fluorine, chlorine or bromine, or represents phenyl, which is optionally substituted up to 3 times in an identical or different manner by fluorine, chlorine, bromine, phenyl, methoxy or nitro, or a salt thereof.

7. The method according to claim 5, wherein in the compounds of formula (I)

$R^1$ represents straight-chain or branched alkyl having up to 4 carbon atoms, which is optionally substituted by methoxy, benzoyl, cyclopropyl, cyclopentyl or cyclohexyl, or represents benzyl, cyclopentyl, cyclohexyl or cycloheptyl, $R^2$ represents fluorine, chlorine, trifluoromethyl or cyano, $R^3$ has the abovementioned meaning of $R^2$ and is identical to or different from this, or represents hydrogen, a and b are identical or different and represent the number 0, 1, 2 or 3, $R^4$ and $R^5$ are identical or different and represent hydrogen, methyl or phenyl, A represents a radical of the formula —CO—O—, —O—CO—, —NH—CO— or —CO—

$R^6$ represents benzyl or represents phenyl which is optionally substituted up to 3 times in an identical or different manner by fluorine, chlorine, phenyl, methoxy or nitro, or a salt thereof.

8. A process for the preparation of a compound of the formula

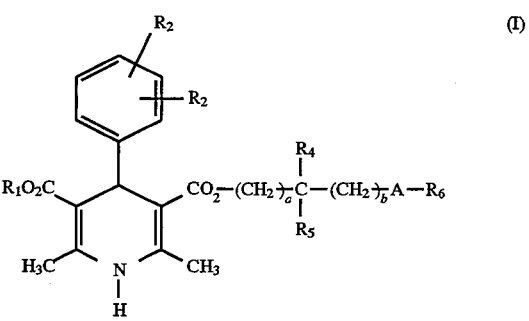

in which $R^1$ represents straight-chain or branched alkyl having up to 8 carbon atoms, which is optionally substituted by straight-chain or branched alkoxy having up to 6 carbon atoms, benzoyl or cycloalkyl having from 3 to 8 carbon atoms, or represents benzyl or cycloalkyl having 3 to 8 carbon atoms, $R^2$ represents halogen, trifluoromethyl or cyano, $R^3$ has the abovementioned meaning of $R^2$ and is identical to or different from this, or represents hydrogen, a and b are identical or different and represent the number 0, 1, 2, 3 or 4, $R^4$ and $R^5$ are identical or different and represent hydrogen, straight-chain or branched alkyl having up to 6 carbon atoms or phenyl, A represents a radical of the formula —CO—O—, —O—CO—, —NH—CO— or —CO—, $R^6$ represents benzyl, which is optionally substituted by halogen, or represents aryl having 6 to 10 carbon atoms, which is optionally substituted up to 3 times in an identical or different manner by halogen, phenyl or nitro or by straight-chain or branched alkoxy having up to 4 carbon atoms, or a salt thereof which comprises

[A] in the case where A represents a —CO— or —CO—O— group, a compound of the formula

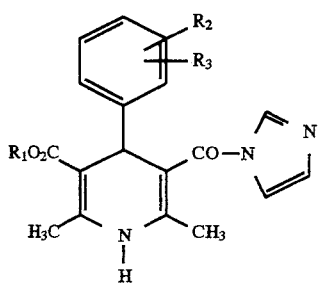

(II)

in which

R¹, R² and R³ have the abovementioned meaning, is reacted with a compound of the formula

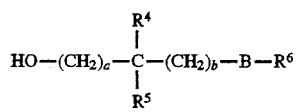

(III)

in which

R⁴, R⁵, R⁶, a and b have the abovementioned meaning and

B represents a —CO— group or represents the —CO—O— group, in an inert solvent, optionally in the presence of a base, or

[B] in the case where A represents a —O—CO— group or —NH—CO— group, a compound of the formula

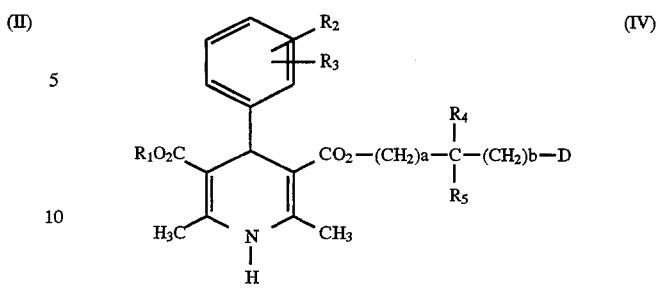

(IV)

in which

R¹, R², R³, R⁴, R⁵, a and b have the abovementioned meaning and

D represents the NH₂ or OH group, is reacted with a compound of the formula

R⁶—CO—E            (V)

in which

R⁶ has the abovementioned meaning and

E, depending on the particular meaning of D, represents halogen or represents hydroxyl, in the presence of an inert solvent optionally in the presence of a base or an auxiliary.

\* \* \* \* \*